United States Patent [19]

Tolpa et al.

[11] Patent Number: 5,290,554
[45] Date of Patent: Mar. 1, 1994

[54] PROCESS FOR THE EXTRACTION OF PEAT AND APPARATUS FOR CARRYING OUT THE PROCESS

[75] Inventors: Stanislaw Tolpa; Tadeusz Gersz; Stanislawa Ritter; Ryszard Kukla; Malgorzata Skrzyszewska; Stanislaw Tomkow, all of Wroclaw, Poland

[73] Assignee: Torf Establishment, Liechtenstein

[21] Appl. No.: 851,670

[22] Filed: Mar. 16, 1992

[30] Foreign Application Priority Data

Mar. 16, 1991 [EP] European Pat. Off. ............ 91104099

[51] Int. Cl.$^5$ ............................................ A61K 35/78
[52] U.S. Cl. ................................................ 424/195.1
[58] Field of Search ............................ 424/195.1; 71/3

[56] References Cited

U.S. PATENT DOCUMENTS

| | | | |
|---|---|---|---|
| 3,903,267 | 9/1975 | Miller et al. | 424/195.1 |
| 4,229,442 | 10/1980 | Pinckard | 424/195.1 |
| 4,272,527 | 6/1981 | Belkevich et al. | 424/195.1 |
| 4,618,496 | 10/1986 | Brasseur | 424/195.1 |

Primary Examiner—John W. Rollins
Attorney, Agent, or Firm—Ostrolenk, Faber, Gerb & Soffen

[57] ABSTRACT

An extracting agent, preferably sodium hydroxide solution containing 0.2 to 0.7% of NaOH, is allowed to flow from bottom to top through a bed of the comminuted peat and is removed above the bed, at a rate such that the flow remains laminar and the extract obtained remains essentially free of entrained particles of the peat to be extracted. If appropriate, fresh extracting agent is added and the extracting agent is allowed to flow once more through the bed, preferably is recirculated several times. An apparatus for carrying out the process has at least one storage tank for the extracting agent (NaOH), at least one extraction tank (E) and at least one circulation tank (Z) for the extracting agent enriched with extract, feed pipes in which pumps (P) are arranged leading both from the storage tank and from the circulation tank (Z) into the lower pipe from each extraction tank (E), while the discharge pipe from each extraction tank (E) leads from its upper part and enters the associated circulation tank (Z).

11 Claims, 2 Drawing Sheets

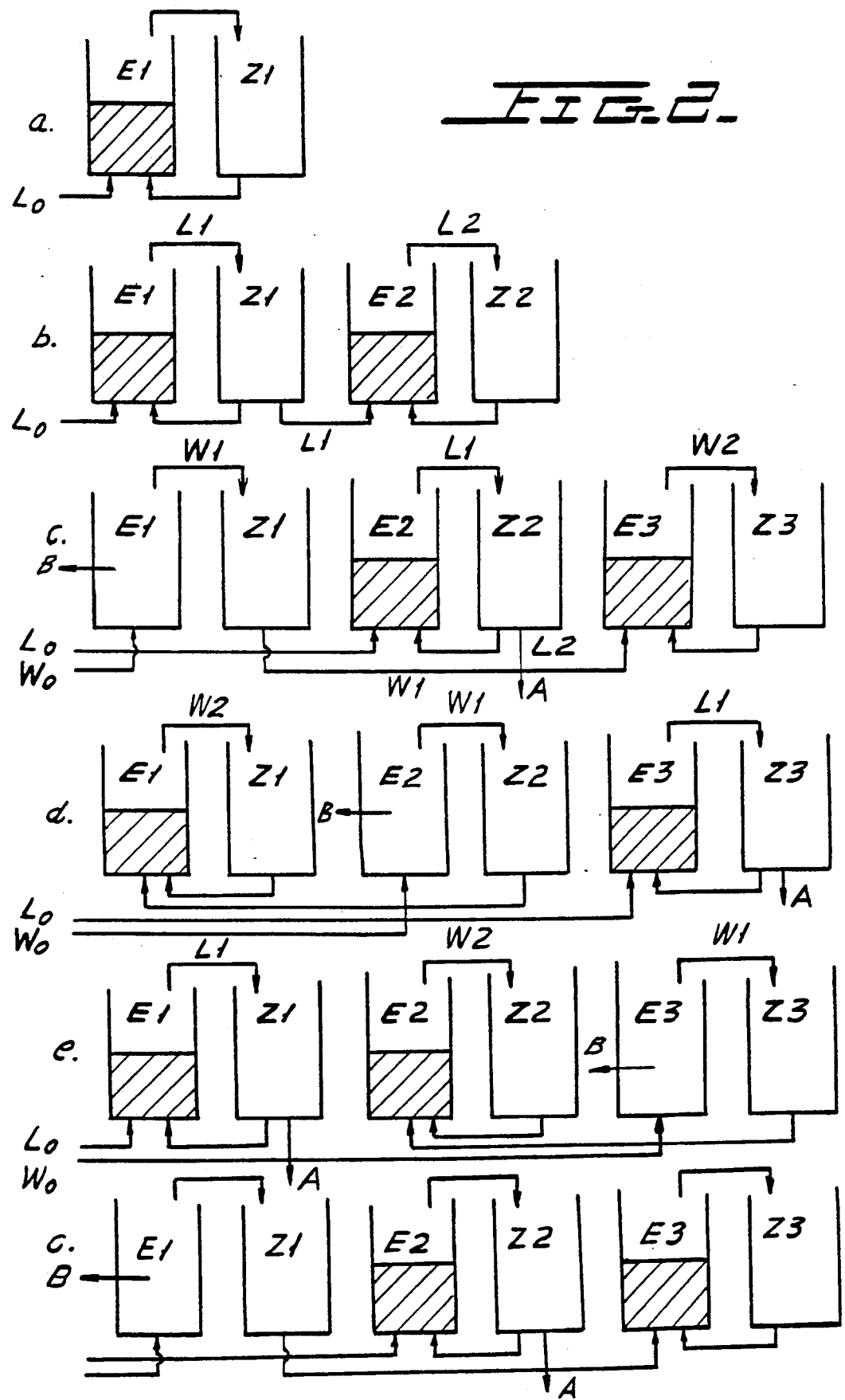

PROCESS FOR THE EXTRACTION OF PEAT AND APPARATUS FOR CARRYING OUT THE PROCESS

Polish patents No 124110 and No. 125769 disclose methods for the processing of peat that lead to the separation of biologically active substances by leaching an air-dried peat with dried aqueous alkaline solutions. Due to the high adsorbing capacity of peat, however, the leaching operation is extremely difficult to carry out on an industrial scale.

The extraction of large quantities of peat in a static way proved to be unsatisfactory. Static extraction is commonly employed to obtain—from crude products having a loose structure and a rather low degree of comminution—extracts that can easily be washed out in batches by means of a suitable extracting solvent. Accordingly, coarsely ground material is flooded with solvent. The extracting fluid is kept in contact with the material for a time sufficient to obtain a saturated solution of the desired substance or substances in the extracting medium, Subsequently, the extract is collected from the bottom of the extractor so that the whole batch of the material is soaked through with the extract. When such a method is applied to a raw, air-dried peat, collection of the extract from the bottom of the extractor is impossible due to the formation of an impermeable mud layer at the bottom parts of the extractor as a result of the sedimentation of swollen peat particles.

For similar reasons a method of soaking peat particles in extracting tubs filled with the extracting solvents, periodical stirring of the mixture and decanting the obtained extract is equally unsuccessful. In such conditions, penetration of the peat with the solvent is very low because the longer the time of contact of the solvent with the peat, the thicker is the impermeable mud layer formed at the bottom part of the extraction tub. Decantation leads to a relatively clear extract, but the concentration of desired substances in such extracts is comparatively low.

More intensive stirring of the mixture increases the penetration of extracting solvent through the peat bed but results in dispersion of the impermeable mud layer and makes impossible the separation of the clear extract by decantation. Sedimentation and swelling of the peat particles cause further problems at the discharge of the extraction tubs and in cleaning them before the next operation cycle. The situation does not improve whether the extracting tubs were filled first with the peat and then the solvent was introduced or when the sequence was reversed, i.e. solvent was poured in first, followed by the addition of peat. Furthermore, the desired active substances diffuse into the extracting solvent from the upper parts of the peat bed only, resulting in a relatively low extraction efficiency. Desired substances present in deeper layers of the peat bed are not dissolved but are discharged with the remaining peat after extraction.

It is an object of the present invention to provide an effective and convenient process for extracting peat and obtaining clear extracts which are both free from any solid particles and rich in the extracted substances. This object is achieved by the measures described below. A further object of the invention is to provide a suitable apparatus for carrying out the extraction process. Further improvements of the invention are achieved by the measures also described below.

According to the present invention, extracting solvent—preferably at ambient temperature and only slightly increased pressure—is fed to the extractor at the bottom and passes through a bed of air-dried peat, under a pressure sufficient to cause free flow of the solvent through the bed. The extract obtained is collected at the top of the extractor above the peat bed, the extract being free from any solid particles. Preferably, the extract obtained is recirculated at least twice and passed through the peat bed in essentially the same conditions.

Inorganic solvents may be used, as an extracting solvent, preferably water and/or aqueous alkaline solutions, such as 0.2–0.7% aqueous solutions of sodium hydroxide, being employed. Although, for economic reasons, extraction is usually carried out at ambient temperatures, even as low as 4° C., higher extracting temperatures may be selected to suit special purposes.

According another embodiment of the invention, organic solvents, such as alcohols, ethers of a higher molecular weight, esters and the like, may be used as extracting solvents, the preferred organic solvent being ethyl alcohol.

The desired degree of extraction is achieved by using fresh extracting solvent in a second stage of extraction, while in both the first and a second stage the extract is recirculated and passed through the peat bed several times.

It is essential in the process according to the present invention that there is a continuous flow of the extracting solvent or recirculated extract, from the bottom to the top layers of the peat particles. As a result, peat particles are suspended in a stream of the solvent going upward but not entrained thereby. Under such conditions, the extracting solvent penetrates the entire peat bed and washes out every single peat particle. This means that the desired substances may thus be extracted from the peat uniformly throughout the entire bed. The time of interaction of the extracting solvent with the peat particles is regulated, both by the flow rate and by recirculating the obtained extract through the peat bed. The final extract obtained by the process is free from any solid particles of the peat, and there is no need for filtration of the extract before further processing of the same.

The inventive effect is achieved by matching the gravitational sedimentation rate of the peat particles with the speed of the extracting liquid moving in the opposite direction. When it is not precisely matched, the particles either sediment or are carried over to the next vessel. The liquid flow is therefore laminar.

The speed of the liquid phase depends on the particle size of the peat and the pressure of feeding the extracting medium, which in turn depends on the height of the peat column in the extractor. At the same time, the quantity of liquid being fed to the extractor depends on the diameter of the extractor and its capacity.

When the operation of the extractor is started, the peat bed is at first loosened by the pressure of liquid so that each peat particle is surrounded from all sides by a liquid phase. No aggregation and no channel-like liquid paths can be observed. Accordingly each particle is extracted in the same way no matter whether it is located at the bottom or top layer of the peat bed.

Some of the numerous advantages resulting from using the present process for extracting peat are the following: the desired substances are almost completely leached out from the peat, the final extract being more concentrated, and therefore, smaller volumes of the extracting solvents may be employed, less energy is needed, and more efficient technical media may be used. In addition to the above, in the preferred embodiment of the invention, when an aqueous solution of sodium hydroxide is used as the extracting solvent, the decrease in the volume of such extracting solvent to be neutralised in further stages of processing results in a significant decrease in the salinity of the final product.

The present invention also relates to a bank of extractors for peat extraction according to the measures described.

Preferably, at least two extractor/circulation tank assemblies, and a storage tank for extracting solvent and at least two assemblies, as well as a collecting tank for the final extract are interconnected with one another via a system of pipes enabling the pumping of liquids from each tank to all the remaining tanks and extractors forming the bank. The extractors are equipped with a feeder for the extracting liquid at the bottom and an extract collecting pipe at the top, respectively below and above the peat bed. Preferably, circulation of the liquids in a bank according to the invention is forced and a bank of extractors is adapted to the operation by feeding the extracting liquids under pressure, with the possibility of continuous regulation of the supply to the pumps.

Preferably, the bank of extractors consists of three such sets extractor/circulation tank, and is operated batchwise in at least a two-stage system.

The bank of extractors according to the invention makes it possible to carry out the extraction in a semi-continuous manner with periodical collection of final extract in pre-set time intervals, which in turn permits regular feeding of the extract to the separate installation (not shown) for further processing the extract and thereby continuously operating the whole production line.

BRIEF DESCRIPTION OF DRAWINGS

FIG. 2a-2e schematically illustrate a possible operating system for the bank.

Figure 1:
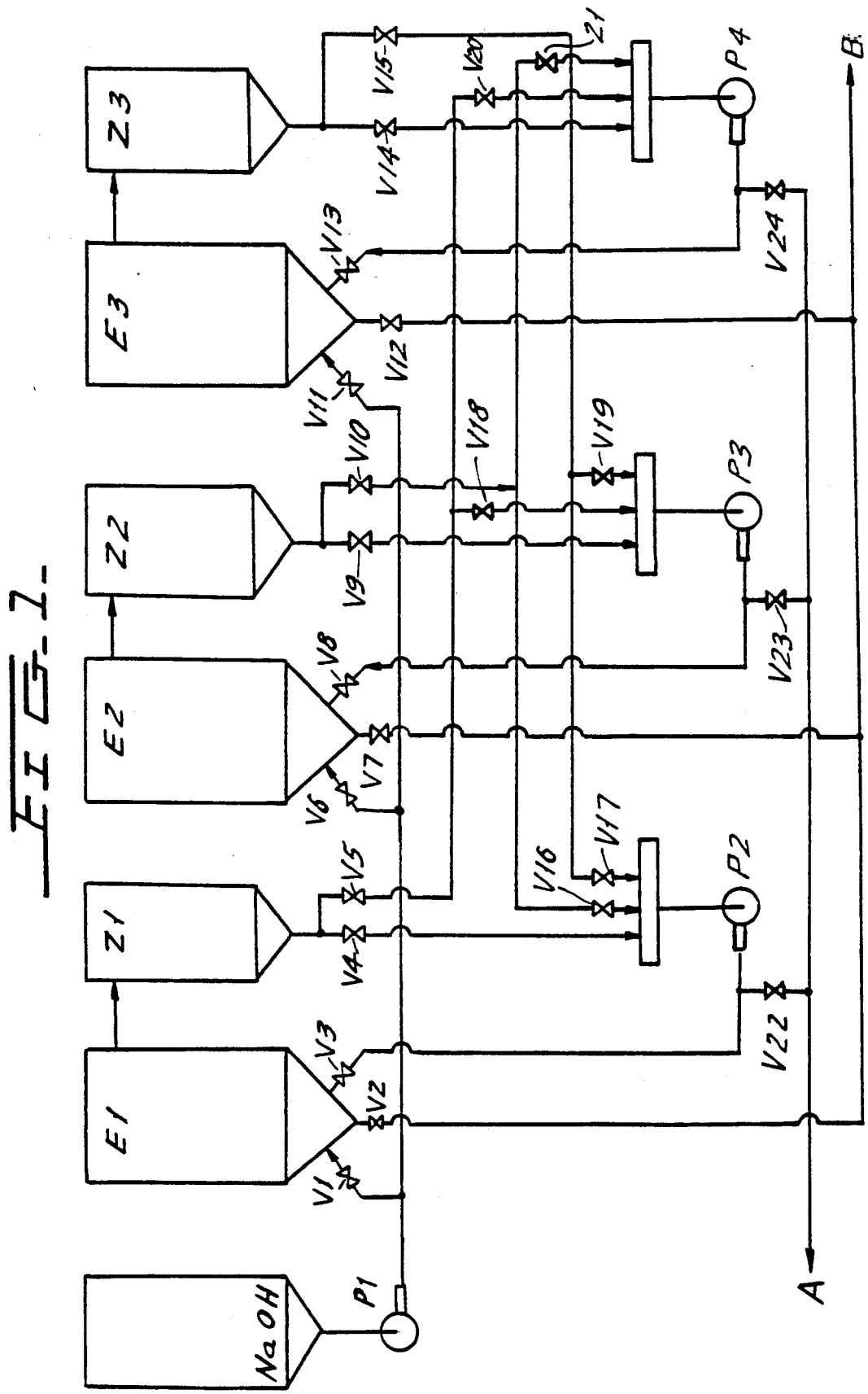
FIG. 1 schematically illustrates all tanks and pip connections (including valves) in the bank of extractors.

The present invention is presented in a detailed manner in the following examples.

EXAMPLE 1

A semi-industrial scale apparatus comprised two glass vessels of 200 liters each and a screw metering pump with continuous regulation of delivery, one of the vessels was used as the extractor and the other one as the circulation tank. The extractor was fed with 90 kg of air-dried peat that had been sieved to result in a particle size of between 8 and 30 mm. Using the metering pump, 300 kg of a 0.35% by weight aqueous solution of sodium hydroxide was fed to the extractor, via a bottom feeding pipe, within about 120 minutes. After the whole volume of the extractor was filled with extracting liquid, the excess of the same passed over to the circulation tank. The outlet pipe was situated above the peat bed level in the extractor. The extracting liquid was subjected to recirculation in a closed cycle between the extractor and the circulation tank approximately eight times, having set the pump supply to 1000 liters per hour. At such a supply rate of the pump, peat particles were kept suspended in a stream of the extracting liquid so that no sedimentation and no aggregation of the peat particles was observed. Accordingly, in the bottom part of the peat bed there was no sign of formation of an impermeable mud layer. At the same time, peat particles did not leave the bed and were not entrained in the liquid passing over to the circulation tank. 175 liters of clear extract was collected. The extract was golden-yellow in colour, indicating a high concentration of the substances extracted from the peat. Depending on the origin of the peat, the extract may contain some or all of the following substances: cellulose, hemicellulose, aminoacid proteins in free structure, resins, waxes, humic acids and their salts, fulvic acids, lignin, hymatomelanic acids, other organic acids, enzymes and others.

EXAMPLE 2

The process according to Example 1 was repeated on an industrial scale.

An extractor was fed with 1000 kg of air-dried peat. 3000 kg of a 0.35% by weight aqueous solution of sodium hydroxide was then introduced into the extractor by a bottom feeding pipe. This extracting liquid passed through the peat bed without entrainment of peat particles on one hand and without allowing aggregation or sedimentation of peat particles in the bottom part of the bed on the other hand. Via an outflow pipe, located above the top level of the peat bed in the extractor, the extracting liquid passed over to the circulation tank. A metering pump suitable for supplying 2 to 8 m3 of liquid per hour was used to feed the extracting liquid to the extractor. The pump was operated at 50 kg/minute. As soon as all the 3000 kg of the liquid was introduced into the system, recirculation was started in order to dynamize the extraction process. The extracting medium was passed through the peat bed approximately eight times, within about eight hours. The resulting extract was removed and replaced with fresh extracting solvent (again 0.35% aqueous solution of sodium hydroxide). A second extraction crop was obtained by recirculating the second portion of extracting liquid under the same conditions as in the first stage of extraction.

The extract resulting from the second stage of extraction was used as an extracting liquid for the next portion of the peat in a first stage of extraction.

EXAMPLE 3

1000 kg of fresh, comminuted and air-dried peat are present in all three extractors E1, E2, E3 (FIG. 1).

a) The pump P1 forces 3000 kg of 0.35% sodium hydroxide solution into the extraction tank E1 and further into the circulation tank Z1; the valve V1 is open.

b) (optional): P2 forces 3000 kg of preladen alkali from Z1—optionally several times—again into E1; the valves V3 and V4 are open.

c) P2 meters the extract-laden alkali—optionally partially—from E1 to further processing (arrow A); the valves V4 and V22 are open.

d) P1 replaces the portion of the optionally removed extract with fresh alkali (valve V1 is open).

An analogous procedure is carried out with extraction tank E2 and circulation tank Z2 and with extraction tank E3 and circulation tank Z3, optionally simultaneously with the above-mentioned steps for E1 and Z1.

EXAMPLE 4 a) The beginning of the procedure is analogous to Example 3a).

b) The pump P3 forces alkali, already laden with extract, from Z1 to E2 and further to Z2; the valves V5, V18 and V8 are open.

c) P3 forces alkali, laden twice, from Z2 to further processing in the direction of arrow A; the valves 9 and 23 are open. Simultaneously, P1 forces fresh alkali to E3 and further to Z3; the valve V11 is open.

d) P2 pumps alkali, laden once, from Z3 to E1 and further to Z1; the valves V15, V17 and V3 are open. The remaining peat is discharged from E2 via valve V7 in the direction of arrow B.

e) E2 is laden with further peat; the cycle is continued again with b) above.

EXAMPLE 5

A certain point in time during batch operation is selected. At this point in time, E1 contains a peat bed through which an alkali laden with a large amount of extract has already flowed once, followed by an alkali laden with a small amount of extract. Fresh alkali now flows through the said bed in order to leach the final residues of extract, after which the bed is replaced by a fresh peat bed.

E2 contains a peat bed through which an alkali laden with a large amount of extract has already flowed once. The alkali which is already laden with some extract and which has passed through E1 now flows through the said bed, followed by fresh alkali.

E3 contains a fresh peat bed through which now flows an alkali laden with a large amount of extract after the latter has passed through the bed in E2. Thereafter, the second (originally fresh) alkali mentioned under E2, which now already contains some extract, is passed over the bed in E3.

An alkali which has already flowed twice through another bed thus first flows through each freshly used peat bed; an alkali which has flowed only once through another bed and then flows through the said bed, through which a fresh alkali finally flows.

After these three passages, the remaining peat mixture is discharged in the direction of arrow B and the extraction tank is, if appropriate, cleaned and charged with a fresh peat bed. Each alkali which has flowed through three beds is pumped to further processing or for slating out (in the direction of arrow A).

A cycle can also be carried out with four or more pairs of extraction tanks/circulation tanks in an analogous manner.

EXAMPLE 6

FIG. 2 shows another procedure using an extraction bank of three extraction tanks E1, E2 and E3 and three circulation tanks Z1, Z2 and Z3. In this case, the process takes place in three cycle steps (2c, 2d and 2e) after an initialisation phase (FIG. 2a to b).

FIG. 2a: Fresh alkali Lo flows through fresh peat in E1, enters the circulation tank Z1 and is optionally recirculated from the latter several times through E1.

FIG. 2b: The partially laden alkali L1 from E1 flows through fresh peat in E2. The resulting alkali L2 enters Z2 and is optionally recirculated several times via E2. At the same time, the partially extracted peat in E1 is treated with further fresh alkali Lo, which in turn is optionally recirculated by Z1.

FIG. 2c: Water Wo now flows through the leached peat in E1 and the peat is then discharged (arrow B). The water W1 which has entered the circulation tank Z1 and is laden with residual materials is now allowed to flow over the fresh peat introduced into E2 and is recirculated as W2 via Z3—if appropriate several times. The peat (already leached once according to FIG. 2b) in E2 is now treated with further fresh alkali Lo, which in turn is recirculated via Z2—if appropriate several times—after the alkali L2 laden twice (from FIG. 2b, Z2) passes in the direction A for further processing such as for salting out.

FIG. 2d: E2 is now washed with water Wo which passes to Z2, the peat is then discharged via B and the water W1 from Z2, which is now laden with residual materials, is allowed to flow through E1 filled with fresh peat. From there, it is recirculated as W2—if appropriate several times—via Z1. At the same time, the peat in E3, which has already been leached once (according to 2c), is treated with fresh alkali Lo and then—if appropriate after repeated recirculation—removed from Z3 via A for further processing.

FIG. 2e: The peat in E1, which has already been preextracted (according to 2d) with preladen water (W1/W2), is now extracted again with fresh alkali Lo, which is removed—if appropriate after repeated circulation—via Z1 and A for further processing. Fresh water Wo now flows over the almost completely extracted peat in E3, the said fresh water being allowed to flow, as W1, partially laden via Z3 and E2 filled with fresh peat, while the washed peat is discharged from E3 via B. The laden water W2 from E2 is recirculated via Z2—if appropriate several times. The cycle then begins again according to FIG. 2c.

The invention is not restricted to the Examples described; thus, the preextraction can also be carried out with an alkali—optionally a dilute alkali—instead of with water; water extraction steps and alkali extraction steps can be carried out alternately; finally, if the procedure is restricted to the switching of valves—it is also possible to employ a virtually completely continuous process by passing the extracting agent counter-current through several extraction tanks, cutting the tank containing the most highly leached peat out of the circulation, emptying it and refilling it.

Effects of Peat Extracts on Improvement of Immunomodulatory and Anticanceractivities Peat extract has already been used with success against the following diseases: paradentosis; cancer and precancerous diseases; autoallergic diseases (for example sclerosis multiple); allergic diseases (for example asthma or dermatitis); various infection diseases (for example influenza); brain- and nerve-tumors (gliomas, astraeyloma); mamma-tumors (carcinoma); bone- and soft part-tumors (mainly sarcoma); leukemia (acute and chronic), lymphatic and myelogenic; lymphomas; hodgkin's disease; head- and neck-tumors; biliary tract-, liver- and pancreas-cancers (carcinoma, adenocarcinoma); tumors of stomach, small intestine, colon and rectum (carcinoma, adenocarcinoma); tumors of kidneys (carcinoma microcellulare, Wilms' disease); cancer of the prostate (adenocarcinoma); testis-tumors (carcinoma, teratoma, chorio-epithelioma); bladder-tumors (carcinoma); tumors of the female genital organs (carcinoma, adenocarcinoma); cancer affected children (Wilms' disease, neuroblastoma, ganglioma).

We claim:

1. Process for the extraction of peat in which the extracting agent is caused to flow through a bed of peat particles from the bottom to the top at such a rate that the flow remains laminar and the extract obtained remains essentially free of entrained particles of the peat to be extracted.

2. Process according to claim 1, wherein the peat has a particle size of between 8 and 30 mm.

3. Process according to claim 1, wherein the flow rate is between 1 and 10 cm/min.

4. Process according to claim 1, wherein the extracting agent laden with the peat ingredients is removed above the bed and allowed to flow at least once more through the bed from the bottom to the top.

5. Process according to claim 4, wherein the extracting agent after removal from above the bed is partially replaced with fresh extracting agent.

6. Process according to claim 4, wherein the extracting agent is recirculated 4 to 8 times.

7. Process according to claim 4, wherein the extracting agent is a 0.2 to 0.7% sodium hydroxide solution.

8. Process according to claim 4, wherein the extracting agent is an organic solvent.

9. Process according to claim 1, wherein the extracting agent used is a 0.2 to 0.7% sodium hydroxide solution.

10. Process according to claim 1, wherein the extracting agent is an organic solvent.

11. Process according to claim 10, wherein the extracting agent is selected from the group consisting of ethyl alcohol, an ester and a high molecular weight ether.

* * * * *